US006967015B1

(12) United States Patent
Burkett

(10) Patent No.: US 6,967,015 B1
(45) Date of Patent: Nov. 22, 2005

(54) DIAGNOSTIC METHOD FOR DETECTING DYSPLASTIC EPITHELIAL TISSUE

(75) Inventor: Douglas D. Burkett, Gilbert, AZ (US)

(73) Assignee: Zila, Inc., Phoenix, AZ (US)

( * ) Notice: Subject to any disclaimer, the term of this patent is extended or adjusted under 35 U.S.C. 154(b) by 327 days.

(21) Appl. No.: 10/069,836

(22) PCT Filed: Jul. 20, 2000

(86) PCT No.: PCT/US00/20017

§ 371 (c)(1),
(2), (4) Date: Nov. 4, 2002

(87) PCT Pub. No.: WO02/07693

PCT Pub. Date: Jan. 31, 2002

(51) Int. Cl.[7] ............................................. A61K 49/00

(52) U.S. Cl. .......................................... 424/9.1; 435/6

(58) Field of Search ..................... 424/9.1, 49; 435/6, 435/7.23; 514/180

(56) References Cited

U.S. PATENT DOCUMENTS

| | | | | |
|---|---|---|---|---|
| 6,086,852 | A | * | 7/2000 | Burkett ........................ 424/9.7 |
| 6,194,573 | B1 | * | 2/2001 | Burkett ........................ 544/37 |
| 6,370,422 | B1 | * | 4/2002 | Richards-Kortum et al. .......................... 600/478 |
| 6,376,525 | B1 | * | 4/2002 | Kong .......................... 514/382 |
| 6,649,144 | B1 | * | 11/2003 | Burkett et al. ............... 424/9.1 |
| 2003/0017158 | A1 | * | 1/2003 | Bernal et al. ............ 424/155.1 |
| 2003/0163049 | A1 | * | 8/2003 | Balas .......................... 600/476 |
| 2004/0146919 | A1 | * | 7/2004 | Burkett .......................... 435/6 |
| 2004/0235067 | A1 | * | 11/2004 | Burkett ..................... 435/7.23 |
| 2005/0014145 | A1 | * | 1/2005 | Burkett .......................... 435/6 |

* cited by examiner

*Primary Examiner*—Ralph Gitomer
(74) *Attorney, Agent, or Firm*—Drummond & Duckworth

(57) ABSTRACT

In diagnostic testing for cancer and precancer of the epithelium, the undesired binding of cancer-selective dyes to proteins in the extracellular matrix, which may lead to false positives, is reduced by applying to the epithelium being tested, before application of the dye, a solution of a non-toxic amphiphilic protein in a pharmacolgically acceptable solvent.

1 Claim, No Drawings

DIAGNOSTIC METHOD FOR DETECTING DYSPLASTIC EPITHELIAL TISSUE

This application is the United States national stage application based on PCT application PCT/US00/20017 (WO 02/07693) filed Jul. 20, 2000.

FIELD OF THE INVENTION

This invention relates to an improved diagnostic method for in vivo detection of dysplastic epithelial tissue.

In a more particular respect, the invention is an improved diagnostic method for detecting and/or delineating cancerous or precancerous epithelial tissue, with a reduced rate of false positives.

According to another aspect of the invention, the false positive rate of diagnostic methods that involve topical application of a dye that selectively stains cancerous and precancerous epithelial tissue is markedly reduced.

These and other, further and more specific aspects of the invention will be apparent to those skilled in the art from the following description thereof.

BACKGROUND OF THE PRIOR ART

It is known that various cationic supravital dyes have the capability of selectively staining cancerous and precancerous cells of epithelial tissue, as well as cells that are abnormal due to dysplasia, hyperplasia, tumorigenesis and other active surface lesions. For example, such dyes are disclosed in U.S. Pat. No. 4,321,251 to Mashberg, U.S. Pat. No. 5,372,801 to Tucci, et al., U.S. Pat. No. 5,882,627 to Pomerantz, and to Bernal U.S. Pat. No. 6,649,144. Also, see Chenz, Chinese Journal of Stomatology (27:44–47)(1992) and Filurin, Stomatologiia (Russian) (72:44–47)(1993). Other dyes that are similarly useful include rhodamine, alcian blue, malachite green, phenosafranin, acriflavine, pyronine Y, toluylene blue, and brilliant green. "Non-dye" compounds that are similarly useful include peonidin, oxythiamine, tiemonium iodide, elliptinium acetate and furazolium chloride.

The mechanism of such selective staining has been shown to involve absorption or entry of the marking agent molecule into the mitochondria of the cancerous or precancerous epithelial cells. This selective staining of the mitochondria of cancerous tissue is apparently due to the higher electrical potential (negative charge on the inside of the membrane of cancerous mitochondrial cells as compared to normal cells.

Although the mitochondrial marking agent also temporarily stains nearby non-cancerous tissue, it is released much more quickly from the normal tissue than from the mitochondria of the cancerous tissue. Thus the diagnosis of cancer is based on the continued retention of the dye in the cancerous tissue after it is autogenously released from the normal tissue. Proper selection of the elapsed time between application of the dye and the diagnostic observation of the tissue, permits the diagnostician to detect and selectively delineate cancerous or precancerous tissue sites on normal epithelial surfaces. This procedure permits identification of cancerous and potential cancerous sites with a high degree of accuracy, i.e., with a very low incidence of false negatives. However, because of differences in the tissues between patients and other variables such as skill of the diagnostician, etc., this diagnostic technique may also yield false positive results.

While false positives are much preferred over false negative results, it would, nevertheless, be highly desirable to reduce the rate of false positives, to avoid or reduce the necessity for invasive confirmatory testing and to avoid unnecessarily upsetting the patient.

To attempt to reduce the rate of false positives, it has been proposed to repeat the procedure after approximately two weeks, which gives time for healing of non-cancerous lesions or wounds which apparently tend to accumulate and retain the dye longer than normal tissue, even though they are not cancerous or precancerous. Of course, this repetition does prevent a number of false positives. However, the potential still remains for false positive due to other causes.

BACKGROUND OF THE INVENTION

The temporary, less pronounced tendency of these dyes to stain normal tissue is due to binding of the dye with components of the extracellular matrix ("ECM") of epithelial tissue. Whereas the dye actually enters the mitochondria of cancerous and precancerous cells, it is only temporarily bound to components of the ECM, particularly to fibronectin.

Temporary binding of cationic dyes and other mitochondrial marking agents to ECM components may be due to one or more of a variety of mechanisms. Thus the mitochondrial marking agents may be temporarily bound to negatively charged ECM proteins by electrostatic attraction. Furthermore, hydrophobic interactions may take place between the ECM proteins and heterocyclic portions of the marking agent which exclude water. Other non-specific binding may occur by binding of various portions of the marking agent to ECM proteins that bind neutral charges. Such temporary binding of mitochondrial marking agents to ECM proteins can occur even outside of the tight junctions between epithelial cells, e.g., on the surface of the epithelium, as well as between and beneath cancerous cells.

DESCRIPTION OF THE INVENTION

The undesired temporary binding of mitochondrial marking agents to ECM proteins can be largely prevented by pretreating the area of the epithelium to which the marking agent is to be applied with a non-toxic amphiphilic protein. The amphiphilic protein enters the various binding mechanisms to the ECM proteins, thus temporarily disabling them from binding the mitochondial marking agent when it is later applied. Such pretreatment of the epithelium with amphiphilic protein markedly reduces the occurrence of false positive reactions engendered by temporary binding of the mitochondrial marking agent to ECM proteins and the consequent appearance of "stained" areas on the normal epithelium which might be mistaken for cancerous or precancerous tissue.

The exact nature of the amphiphilic protein to be applied as a pretreatment is not highly critical. All mucopolysaccharides are amphiphilic. However, for ease of handling and application, it is presently preferred to employ albumins (soluble in water) or globulins (soluble in dilute salt solutions). For example, serum albumin and milk proteins, such as casein, are effectively employed. Gluten proteins, such as wheat albumins and prolamins (soluble in aqueous alcohol) and glutenins (soluble in dilute acids and bases, detergents or reducing agents) are also effectively employed.

The following examples illustrate the presently preferred practice of the invention. Those skilled in the art will understand and appreciate modifications of this procedure that can be made without departing from the basic concept

WORKING EXAMPLES

Example 1

Preparation of Pre-Treatment Composition

The following amphiphilic protein pre-treatment composition is prepared:

| Component | Weight % |
|---|---|
| Serum albumin | 30 |
| Sterile water | 68.5 |
| Flavor (IFF Raspberry IC563457) | .5 |
| Preservative (sodium benzoate) | 1.0 |

Example 2

Preparation of TBO Stain Composition

A toluidine blue O ("TBO") stain composition is prepared, having the following composition

| Component | Weight % |
|---|---|
| TBO | 1.00 |
| Flavor (IFF Raspberry IC563457) | .20 |
| Buffering Agent (sodium acetate trihydrate) | 2.45 |
| Preservative (hydrogen peroxide 30%) | .41 |
| Acetic acid | 4.61 |
| Ethyl alcohol | 7.48 |
| Water | 83.85 |

Example 3

Preparation of Pre-Rinse and Post-rinse Solutions

Pre-rinse and post-rinse solutions of 1 wt % acetic acid in purified water, sodium benzoate preservative and raspberry flavor are prepared.

Example 4

Clinical Protocol

The patient is draped with a bib to protect clothing. Expectoration is expected, so the patient is provided with a 10-oz. cup, which can be disposed of in an infectious waste container or the contents can be poured directly into the center drain of a sink to avoid staining the sink. Environmental surfaces or objects which might be stained are draped or removed from the area.

A visual oral cancer examination is conducted, without using any instruments which might cause nicks or cuts of soft tissues. Notations are made of the appearance of soft tissues and teeth.

The patient rinses the oral cavity with approximately 15 ml of the of the pre-rinse solution for approximately 20 seconds and expectorates, to remove excess saliva and provide a consistent oral environment. This step is then repeated with additional pre-rinse solution.

The patient then rinses and gargles with water for approximately 20 seconds and expectorates.

The patient then rinses and gargles with approximately 50 ml of the protein pretreatment composition for approximately 30 seconds and expectorates. This step is then repeated, except that the patient retains the protein pretreatment composition within the mouth for approximately two minutes, then expectorates.

The patient then rinses and gargles with 30 ml. of the TBO solution for one minute and expectorates.

The patient then rinses with 15 ml of the post rinse solution and expectorates. This step is then repeated.

The patient then rinses and gargles with water for 20 seconds and expectorates. This step is then repeated.

Visual observations of the oral cavity are then made, using appropriate soft-tissue examination techniques, including retraction, well-balanced lighting and magnification, if necessary. The location, size, morphology, color and surface characteristics of suspect lesions, that have retained blue coloration are made and recorded.

Specimens of any tissues that have retained blue coloration are obtained and subjected to normal cancer-detection histological procedures. No "false positives" specimens are noted.

Example 5

Use of Other Proteins

The procedures of Examples 1–4 are repeated except that the protein pre-treatment solution of Example 1 consists of globulins, casein, gluten albumin, wheat prolamin and glutenins in suitable pharmacologically acceptable solvents, with suitable flavorings.

Equivalent results are obtained.

Example 6

Use of Other Mitochondrial Marking Dyes

The procedures of Examples 1–5 are repeated except that the staining dyes employed are Azure B, Azure C, Brilliant Cresyl Blue, Rhodamine, Alcian Blue, Malachite Green, Phenosafranin, Acriflavine, Pyronine Y, Toluylene Blue, Brilliant Green, Peonidin, Oxythiamine, tiemonium iodide, elliptinium acetate and furazolium chloride.

Equivalent results are obtained.

Having described my invention in such terms as to enable those skilled in the art to understand and practice it and, having identified the presently preferred embodiments thereof,

I claim:

1. In a diagnostic method for detecting dysplastic epithelial tissue, which diagnostic method includes the step of
topically applying a mitochondrial marking agent, which selectively stains mitochondria of cancerous and precancerous cells, to a locus of suspect tissue, said locus comprising epithelial cells and extracellular matrix, said matrix being subject to temporary staining by said agent, thereby leading to possible false positive results of said diagnostic method, the improvement in said diagnostic method for decreasing false positive results of said method, said improvement comprising the step of inhibiting the staining of said extracellular matrix in said locus by said marking agent, by topically applying to said locus, prior to applying said marking agent to said locus, a solution of a non-toxic amphiphilic protein in a pharmacologically acceptable solvent.

* * * * *